(12) United States Patent
Choi et al.

(10) Patent No.: US 9,945,841 B2
(45) Date of Patent: Apr. 17, 2018

(54) CELL CYCLE MEASURING METHOD BASED ON AN ELECTROCHEMICAL METHOD

(75) Inventors: Jeong-Woo Choi, Seoul (KR); Tae-Hyung Kim, Gyeonggi-do (KR); Kafi Md Abdul, Seoul (KR)

(73) Assignee: INDUSTRY-UNIVERSITY COOPERATION FOUNDATION SOGANG UNIVERSITY, Seoul (KR)

( * ) Notice: Subject to any disclaimer, the term of this patent is extended or adjusted under 35 U.S.C. 154(b) by 1151 days.

(21) Appl. No.: 13/982,286

(22) PCT Filed: Jan. 25, 2012

(86) PCT No.: PCT/KR2012/000588
§ 371 (c)(1),
(2), (4) Date: Oct. 9, 2013

(87) PCT Pub. No.: WO2012/102545
PCT Pub. Date: Aug. 2, 2012

(65) Prior Publication Data
US 2014/0024044 A1 Jan. 23, 2014

(30) Foreign Application Priority Data
Jan. 28, 2011 (KR) .......................... 10-2011-0008706

(51) Int. Cl.
*G01N 33/50* (2006.01)
*G01N 33/569* (2006.01)

(52) U.S. Cl.
CPC ..... *G01N 33/5008* (2013.01); *G01N 33/5011* (2013.01); *G01N 33/56966* (2013.01)

(58) Field of Classification Search
CPC .......... G01N 33/5008; G01N 33/5011; G01N 33/56966
(Continued)

(56) References Cited

U.S. PATENT DOCUMENTS 5,149,630 A * 9/1992 Forrest ............... G01N 33/5438
204/403.1
5,278,048 A * 1/1994 Parce ..................... C12M 35/08
422/81
(Continued)

FOREIGN PATENT DOCUMENTS

KR 10-2004-0063058 A 7/2004
KR 10-2006-0124450 A 12/2006
(Continued)

OTHER PUBLICATIONS

Wang et al., "Real-time, label-free monitoring of the cell cycle with a cellular impedance sensing chip", Biosensors & Bioelectronics (2010) 25:990-995.*
(Continued)

*Primary Examiner* — Scott Long
*Assistant Examiner* — Gary E Hollinden
(74) *Attorney, Agent, or Firm* — Harness, Dickey & Pierce, P.L.C.

(57) ABSTRACT

A method for measuring cell cycles includes immobilizing a capture specifically binding to a cell membrane protein to a substrate, wherein the cell membrane protein is a counterpartner binding to the capture, binding a cell having the cell membrane protein as the counterpartner to the capture, and measuring a redox potential of the cell. A method for screening a substance affecting cell cycles includes immobilizing a capture specifically binding to a cell membrane protein to a substrate; wherein the cell membrane protein is a counterpartner binding to the capture, binding a cell having the cell membrane protein as the counterpartner to the capture, treating a test substance of interest for analysis to a cell, and measuring a redox potential of the cell.

12 Claims, 11 Drawing Sheets

(58) Field of Classification Search
USPC ........................................................ 436/518
See application file for complete search history.

(56) References Cited

U.S. PATENT DOCUMENTS

| | | | | |
|---|---|---|---|---|
| 6,942,771 | B1* | 9/2005 | Kayyem | ............... B01L 3/5027 |
| | | | | 204/409 |
| 2001/0012620 | A1 | 8/2001 | Rich | |
| 2002/0010946 | A1* | 1/2002 | Meyers | ................ C12N 9/0006 |
| | | | | 800/8 |
| 2002/0012943 | A1* | 1/2002 | Fowlkes | ................ B82Y 30/00 |
| | | | | 435/7.1 |
| 2004/0180377 | A1* | 9/2004 | Manger | ............... B01L 3/50273 |
| | | | | 435/7.1 |
| 2006/0105407 | A1 | 5/2006 | Lee et al. | |
| 2007/0232701 | A1* | 10/2007 | Griguer | ................. A61K 31/12 |
| | | | | 514/688 |
| 2007/0292406 | A1* | 12/2007 | Kang | ..................... A61K 38/44 |
| | | | | 424/94.4 |
| 2008/0038755 | A1* | 2/2008 | Kauvar | .................. C07K 16/00 |
| | | | | 435/7.32 |
| 2009/0226931 | A1* | 9/2009 | Bunch | .................... C12Q 1/025 |
| | | | | 435/7.1 |
| 2009/0260995 | A1* | 10/2009 | Warriner | .......... G01N 33/56961 |
| | | | | 205/778.5 |
| 2011/0071038 | A1* | 3/2011 | Ermantraut | ....... B01L 3/502707 |
| | | | | 506/9 |
| 2011/0166034 | A1* | 7/2011 | Kwong | ................ C12Q 1/6834 |
| | | | | 506/9 |

FOREIGN PATENT DOCUMENTS

| | | |
|---|---|---|
| KR | 10-2006-0134264 A | 12/2006 |
| KR | 10-2008-0057113 A | 6/2008 |

OTHER PUBLICATIONS

International Search Report for PCT/KR2012/000588.

* cited by examiner

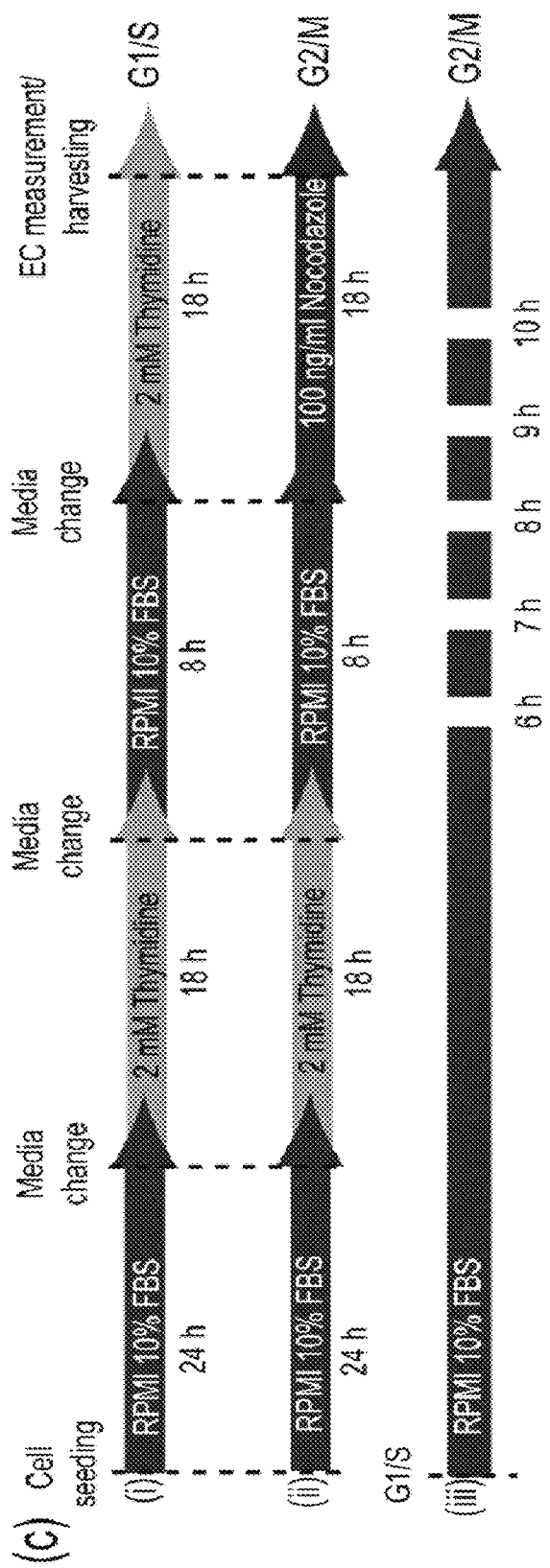

CELL CYCLE MEASURING METHOD BASED ON AN ELECTROCHEMICAL METHOD

CROSS REFERENCE TO RELATED APPLICATIONS AND CLAIM OF PRIORITY

This application is a national phase application of PCT Application No. PCT/KR2012/000588, filed 25 Jan. 2012, which claims priority to Korean Patent Application No. 10-2011-0008706 filed 28 Jan. 2011, the entire contents of which are incorporated herein by reference.

FIELD OF THE INVENTION

The present invention relates to a method for determining cell cycle phase.

DESCRIPTION OF THE RELATED ART

The cell cycle is a ubiquitous spontaneous process involving the growth and proliferation of cells that is essential to organism development. Cells tend to show cycle-dependent characteristics, which are defined by a sequence of events in which several specific nuclear changes occur (1). Many complex stages comprise the cell cycle; however, based on morphological changes, the cell cycle can be broadly subdivided into inter-phase and mitotic (M)-phase stages (2). The M-phase includes several sub-phases, including prophase, metaphase, anaphase, and telophase (2). Similarly, inter-phase encompasses the G1, S, and G2-phases, where the G1 and G2-phases represent "pauses" in the cell cycle that occur between DNA synthesis and mitosis (3). The G1-phase is the first pause in which cells prepare for DNA synthesis. In the S-phase, cells synthesize DNA and thus have an aneuploidic DNA content between 2N and 4N (4). Conversely, the G2-phase is the second pause of the cell cycle in which the cell prepares for mitosis (M-phase). Based on the cell cycle stages, checkpoints for DNA damage are classified into three stages: G1/S (G1), intra-S phase, and G2/M checkpoints (5).

Artificial regulation of the cell cycle is very important in cell-based research since cells in different stages react differently even when maintained under the same environmental conditions. Since cells are unsynchronized in their natural state, non-toxic specific materials are essential for cell synchronization. Thymidine and nocodazole are potential regulators of cell cycle arrest (6-10), and have been used to identify and separate cells in different stages by fluorescence-activated cell sorting (FACS) assay (11-13), imaging using molecular probes (9-10), and Western blot analysis using cell cycle-dependent proteins (14). However, all of these methods inevitably require conjugation of fluorescent probes for cell sorting, which is time-consuming, laborious, and expensive. For these reasons, electrochemical impedance sensing was recently introduced as a new tool for monitoring cell cycle progression (22). This impedance-based technique was proved to be a tool that is useful for the simple and easy detection of effects of thymidine on the cell cycle progression by eliminating the external dyes or devices essential for conventional methods. However, cells in different cell cycle stages could not be clearly differentiated due to the limitation of the technique which only detects the impedance between cells and electrode surfaces. Therefore, a simple and rapid method with high sensitivity is still of great interest for the confirmation of cell cycle arrest.

Throughout this application, various publications and patents are referred and citations are provided in parentheses. The disclosures of these publications and patents in their entities are hereby incorporated by references into this application in order to fully describe this invention and the state of the art to which this invention pertains.

SUMMARY

The present inventors have made intensive studies to develop a method for efficient, prompt, and high-sensitivity determination of cell cycle phase from electrochemical signals using the property of cells exhibiting different electrochemical signals depending on the type of cell lines. As results, the present inventors have found that the cell cycle phase can be more conveniently determined with high sensitivity by: immobilizing a capture agent on a substrate wherein the capture agent specifically binds to a cell membrane protein and wherein the cell membrane protein is a binding partner to the capture agent; binding a cell having the cell membrane protein as the binding partner to the capture agent; treating the cell with a cell cycle synchronizing agent; and measuring a redox potential of the cell, and thus have completed the present invention.

Accordingly, it is an object of this invention to provide a method for determining cell cycle phase.

It is another object of this invention to provide a method for screening a substance affecting cell cycle phase.

It is still another object of this invention to provide a screening method to elucidate whether a test substance of interest affects cell cycle phase, using the measurement of a redox potential of the cell.

Other objects and advantages of the present invention will become apparent from the following detailed description together with the appended claims and drawings.

In one aspect of this invention, there is provided a method for determining cell cycle phase, the method comprising:

(a) immobilizing a capture agent on a substrate wherein the capture agent specifically binds to a cell membrane protein and wherein the cell membrane protein is a binding partner to the capture agent;

(b) binding a cell having the cell membrane protein as the binding partner to the capture agent;

(c) treating the cell with a cell cycle synchronizing agent; and (d) measuring a redox potential of the cell, wherein the step (d) is performed by a differential pulse voltammetry using a tri-electrode consisting of a working electrode, a reference electrode, and a counter electrode, and wherein where a peak was observed only at 50 mV in the redox potential, the cell cycle phase is determined to be in the G1/S phase; where a peak was observed only at 150 mV in the redox potential, the cell cycle phase is determined to be in the G2/M phase; where peaks were observed at 50 mV and 150 mV in the redox potential, if the magnitude of the peak at 50 mV decreases and the magnitude of the peak at 150 mV increases with time, the cell cycle phase is determined to be in the transition from G1/S to G2/M phase is in progress; if the magnitude of the peak at 50 mV increases and the magnitude of the peak at 150 mV decreases, the cell cycle phase is determined to be in the transition from G2/M to G1/S is in progress.

The present inventors have developed cell-chip technology which can effectively measure the changes in cell viability upon exposure to different types of environmental toxins (15, 16) or anticancer drugs (17, 18) based on simple and rapid electrochemical techniques. The electrical or electrochemical manner was also combined with cell-based sensor arrays (19), as in an electrical sensor device for finding signal frequency patterns generated from cells in growth medium (20, 21). Based on previous research, the present inventors have found an oxidation-reduction reaction in a cell-electrode interface which determines the physiological characteristics of target cells (15). The oxidation-reduction reaction varies depending on the type of cell lines (15-18). Since different types of cell lines respectively represent different electrochemical signals, the present inventors have assumed that the same cell lines in different cell cycle stages will represent different electrochemical signals. Therefore, the present inventors have decided that the findings may be used for determining cell synchronization as potential non-labeled techniques.

As describe above, the present inventors have made intensive studies to develop a method for efficient, prompt, and high-sensitivity determination of cell cycle phase using cell property exhibiting different electrochemical signals depending on the type of cell lines. As results, the present inventors have found that the cell cycle phase can be more conveniently determined with high sensitivity by: immobilizing a capture agent on a substrate wherein the capture agent specifically binds to a cell membrane protein and wherein the cell membrane protein is a binding partner to the capture agent; binding a cell having the cell membrane protein as the binding partner to the capture agent; treating the cell with a cell cycle synchronizing agent; and measuring a redox potential of the cell.

Each step of the present invention will be described in detail as follows:

Step (a): Immobilizing a Capture Agent on a Substrate

According to the present method, first, a capture agent specifically binding to a cell membrane protein is immobilized on a substrate.

The term used herein "capture agent" refers to a substance which is bound to a cell membrane protein to immobilize the cell.

According to a preferred embodiment, the capture agent is a peptide, a protein, an antibody, or an aptamer.

Preferably, the antibody as the capture agent specifically binding to a certain cell membrane protein is a polyclonal or monoclonal antibody, and more preferably a monoclonal antibody. In addition, the antibody as the capture agent specifically binding to a certain cell membrane protein includes an antigen binding fragment as part of the antibody.

The antibody may be produced by a method widely known in the art, such as a hybridoma method (Kohler and Milstein, *European Journal of Immunology*, 6:511-519 (1976)), a recombinant DNA method (U.S. Pat. No. 4,816,56), or a phage antibody library technique (Clackson et al, *Nature*, 352:624-628(1991) and Marks et al, *J. Mol. Biol.*, 222:58, 1-597(1991)). General processes for antibody production are described in Harlow, E. and Lane, D., *Using Antibodies: A Laboratory Manual*, Cold Spring Harbor Press, New York, 1999; Zola, H., *Monoclonal Antibodies. A Manual of Techniques*, CRC Press, Inc., Boca Raton, Fla., 1984; Coligan, *CURRENT PROTOCOLS IN IMMUNOLOGY*, Wiley/Greene, N Y, 1991, and the literature is inserted as reference in the present invention. For example, the preparation of the hybridoma cells producing monoclonal antibody is accomplished by fusing immortalized cell line into antibody-producing lymphocytes. The technology required for this process is widely known in the art and may be easily carried out. Polyclonal antibodies may be produced by injecting the protein antigen into an appropriate animal, collecting blood samples from the animal, and then obtaining sera containing antibodies using affinity technology known in the art.

Preferably, the aptamer as the capture agent specifically binding to a certain cell membrane protein is a peptide aptamer. General descriptions of the aptamer are described in Bock L C et al., *Nature* 355 (6360): 564-6 (1992); Hoppe-Seyler F, Butz K "Peptide aptamers: powerful new tools for molecular medicine". *J Mol Med*. 78 (8): 426-30 (2000); Cohen B A, Colas P, Brent R. "An artificial cell-cycle inhibitor isolated from a combinatorial library". *Proc Natl Acad Sci USA*. 95 (24): 14272-7 (1998), and the literature is inserted as reference in the present invention. The aptamer may be obtained by SELEX (Systemic Evolution of Ligands by Exponential Enrichment) (Tuerk and Gold, Science, 249:505-510(1990)).

The capture agent is immobilized on a solid-phase substrate. The term used herein "substrate" encompasses metal substrates such as gold, silver, copper, platinum, aluminum, alloys thereof (for example, an alloy of gold and copper) or metal oxide substrates and silicon, metal film substrates, glass substrates, thin glass substrates, and plastic substrates such as polyimide (PI) substrate, polyethylenenaphthalate (PEN) substrate, polyethylene terephthalate (PET) substrate, polycarbonate (PC) substrate, polyethersulfone (PES) substrate, preferably metal substrates, and most preferably gold (Au) substrates. The term used herein "Au substrate" encompasses a substrate coated with gold. The Au substrate is capable of binding with a capture agent more effectively, as compared to other metal substrates.

Step (b): Binding a Cell Having the Cell Membrane Protein as the Binding Partner to the Capture Agent After the immobilization of the capture agent on the substrate, a cell having the cell membrane protein as the binding partner is bound to the capture agent.

Since the capture agent is an affinity molecule specifically binding to the cell membrane protein, the binding is achieved by treating the cell with the capture agent immobilized on the substrate.

The cell membrane protein mediating the binding between the capture agent and the cell includes any protein known in the art.

According to a preferred embodiment, the cell membrane protein is a membrane receptor, and most preferably an integrin.

The integrin is a heterodimer containing two distinct chains, called α (alpha) and β (beta) subunits. In mammals, eighteen α subunits and eight β subunits have been characterized, whereas the *Drosophila* genome encodes only five α subunits and two β subunits. Biological functions of the integrin are classified into attachment with the extracellular matrix and signal transduction. First, the attachment with the extracellular matrix means a binding with the ligands of the integrin. The ligands of the integrin are fibronectin, vitronectin, collagen, and laminin. The connection between the cell and the extracellular matrix may help the cell to endure pulling forces without being ripped out of the extracellular matrix. Second, the integrin plays an important role in cell signaling. Connection with extracellular matrix molecules can cause a signal to be relayed into the cell through protein kinases that are indirectly and temporarily connected with the intracellular end of the integrin molecule, likely following shape changes directly stimulated by extracellular matrix binding. The signals that the cell receives through the integrin may have a relation to cell growth, cell division, cell survival, cellular differentiation, and apoptosis.

In the present invention, the binding to the ligands of the present integrin in the biological characteristic of the integrin is used, whereby reagent treatments or electrochemical measurements may be performed more stably and effectively by immobilizing cells on the substrate using the binding to the capture agent immobilized on the substrate.

In the present invention, where a cell having the integrin as the cell membrane protein is used, the capture agent is preferably a peptide specifically binding to the integrin. More preferably, the capture agent is a peptide containing essentially "Arg-Gly-Asp (RGD)". Still more preferably, the capture agent is the RGD-containing peptide represented by General Formulae 3 and 4 as described in the Republic of Korea Patent No. 894,703, and most preferably the RGD-containing peptide as described in FIG. 9.

Step (c): Measuring a Redox Potential of the Cell

Finally, a redox potential of the cell immobilized on the substrate is measured to analyze a cell cycle phase.

The term used herein "redox potential" is also called ORP (Oxidation-Reduction Potential), and represents the tendency of a chemical species to gain electrons to be reduced, or to lose electrons to be oxidized. The measurement of the redox potential is carried out by measuring a potential that is generated by injecting an inert sensing electrode into aqueous solutions in an oxidation-reduction reversible equilibrium state. The redox potentials of aqueous solutions in which oxidation and reduction materials exist (e.g., Fe (III) ion $Fe^{3+}$ and Fe (II) ion $Fe^{2+}$, or oxygen and water) are determined by measuring the potential difference between an inert sensing electrode (e.g., platinum, gold, and graphite) in contact with the solution and the standard hydrogen electrode connected to the solution, because the accurate absolute potentials are difficult to measure.

The parameter for determining the redox potential includes the standard electrode potential, the standard reduction potential, and the electrochemical potential.

According to a preferred embodiment, the present redox potential is the electrochemical potential.

The cell membrane proteins inherent to the membrane systems of cell membranes or cell organelles may be useful in vivo by exchanges between the electrochemical potential difference and another form of energy. The electrochemical potential difference is converted from chemical reaction energy or light energy by electron transfer systems, various ATPases, and bacteriorhodopsin. Once the electrochemical potential difference is generated, the electrochemical potential difference is converted into the electrochemical potential difference of different ions or the chemical potential difference of neutral molecules by membrane protein as a transporter, thereby maintaining active transport of useful substances in vivo and homeostasis (e.g., intracellular ion composition).

In addition, the generated electrochemical potential difference ranges to approximately 200 mV, leading to several kcal·mol$^{-1}$, and energy compounds may be synthesized in vivo using electrochemical potential differences like oxidative phosphorylation and photophosphorylation. The electrochemical potential differences of various ions (particularly, cation) are generated at both sides of the membrane, and the electrochemical potential difference of hydrogen ions is the most widely used electrochemical potential difference in biological systems.

A method for measuring the electrochemical potential difference of interest for analysis in the present invention includes Differential Pulse Voltammetry (DPV), Polarography, Cyclic voltammetry, Linear sweep techniques, chronoamperometry, Chronopotentiometry, Square wave voltammetry, and most preferably Differential Pulse Voltammetry. Differential Pulse Voltammetry is different from general pulse voltammetry in terms of reading the pulse continuity. Differential Pulse Voltammetry is characterized in that potential changes are detected, and expressed as a function.

According to a preferred embodiment, DPV is performed using a tri-electrode consisting of a working electrode, a reference electrode and a counter electrode.

The working electrode refers to the electrode in an electrochemical system on which the reaction of interest is occurring. The working electrode is often used in conjunction with the counter electrode, and may be used either cathodically or anodically. The working electrode may consist of inert metals such as gold, silver, and platinum, inert carbon such as glassy carbon or pyrolytic carbon, and mercury drops.

The reference electrode is an electrode which has a stable and well-known electrode potential. The reference electrode is a standard in measurements of the potential difference, and is used to measure the potential difference from the working electrode. The standard hydrogen electrode is the reference from which all standard redox potentials are determined and has been assigned 0.0 mV to define the relative potential difference. A counter electrode also called an auxiliary electrode uses stable materials such as platinum, gold, and graphite to minimize resistances depending on the current because the resistance should be considered in the accurate measurement of potentials.

As mentioned above, the cell cycle phase of a cell of interest for analysis may be determined by measuring the redox potential of the cells immobilized on the substrate. In other words, since every cell cycle phase represents a unique redox potential, the cell cycle phase may be analyzed by measuring the redox potential of the cells immobilized on the substrate.

According to a preferred embodiment, the method further comprises a step of treating the cell with a cell cycle synchronizing agent between the steps (b) and (c). In the present invention, the cells must be treated with a cell cycle synchronizing agent to determine the cell cycle phase by measuring G1/S phase- and G2/M phase-specific signals. The term used herein "cell synchronization" refers to a process by which the cells at different phases of the cell cycle are brought to the same phase, and the cell synchronization is required to study the progression of cells through the cell cycle. The term "cell cycle synchronizing agent" refers to a reagent used for making cells be in the same cell cycle phase.

Tissues typically contain a large number of cells and each cell has independently a cell cycle, whereby there are cells in unsynchronized interphase, metaphase, anaphase and telophase. Therefore, when the electrochemical signals are measured by DPV under circumstance without treatment with the cell cycle synchronizing agent, signals of all cell cycle phases indiscriminately appear such that it is difficult to detect the phase-specific signals. In order to detect G1/S phase- and G2/Mphase-specific signals in the present invention, most of cells cultured in media are treated with a cell cycle synchronizing agent capable of synchronizing the G1/S phase and the phase is blocked. The same applies to the G2/M phase. To synchronize cells, inhibitory metabolic pathways of cell cycles are used. The inhibitory metabolic pathways of cell cycles are used in two manners, and the first manner is to inhibit a certain cell cycle phase. For example, where cells are treated with thymidine or aphidicolin under serum starvation, the cells are blocked at the G1-phase. Where cells are treated with colchicine or nocodazole under serum starvation, the cells are blocked at the M-phase. Where cells are treated with 5-fluorodeoxyuridine under serum starvation, the cells are blocked in the S-phase. In order to synchronize cells at the G1/S phase and the G2/M phase in the present invention, cells were treated with thymidine and nocodazole to block the progression of cell cycle at the corresponding phases, respectively. Therefore, where cells are synchronized at G1/S- or G2/M-phase, the phase-specific signals are detected, respectively. In addition, reagents corresponding to the phase may be used to detect the phase-specific signals.

According to a preferred embodiment, the cell cycle synchronizing agent is thymidine, aphidicolin, colchicine, nocodazole or 5-fluorodeoxyuridine.

In order to analyze influences on the cell cycle, where the conventional methods are used to identify and separate cells in different stages by fluorescence-activated cell sorting (FACS) assay, imaging using molecular probes, and performing Western blot analysis using cell cycle-dependent proteins, the methods are time-consuming, laborious, and expensive. However, since the DPV method may immediately detect relevant signals using probes so long as there is a time sufficient to occur cell synchronization, the DPV method may be very fast, easy, and economical.

As demonstrated in the following Examples, the present method for determining cell cycle phase using the present DPV shows very fast and economical measurement results as compared with the conventional methods for determining cell cycle phase. Through these properties, the measurement results of the cell cycle phase may be immediately obtained using the method for determination.

According to a preferred embodiment, the method further comprises a step of treating the cell with a test substance of interest for analysis between the steps (b) and (c). Alternatively, the method further comprises a step of treating the test with a test substance of interest for analysis of whether the test substance affects the cell cycle phase prior to the step (b). Therefore, it may be quickly and efficiently analyzed whether the test substance affects cell cycle.

In another aspect of this invention, there is provided a method for screening a substance affecting cell cycles, comprising:

(a) immobilizing a capture agent on a substrate wherein the capture agent specifically binds to a cell membrane protein and wherein the cell membrane protein is a binding partner binding to the capture agent;

(b) binding a cell having the cell membrane protein as the binding partner to the capture agent;

(c) treating the cell with a test substance of interest for analysis; and (d) measuring a redox potential of the cell, wherein the step (d) is performed by a differential pulse voltammetry using a tri-electrode consisting of a working electrode, a reference electrode, and a counter electrode, and wherein when the test substance changes the redox potential compared to the redox potential of a cell treated with a cell cycle synchronizing agent, the test substance is determined to be a substance affecting cell cycles.

Since the present method is virtually the same as the method for analyzing cell cycle phase except for treatment with a test substance, the overlapping descriptions between the two are omitted in order to avoid undue redundancy leading to the complexity of this Specification.

The test substance of interest for analysis in the present invention includes various substances. For example, the test substance to be used in the present invention is a single compound or a mixture of compounds (e.g., natural extract, or cell or tissue culture). The test substance may be obtained from libraries of synthetic or natural compounds. The method has been known in the art. The synthetic compound library may be purchased from Maybridge Chemical Co. (UK), Comgenex (USA), Brandon Associates (USA), Microsource (USA) and Sigma-Aldrich (USA), and the natural compound library may be purchased from Pan Laboratories (USA) and MycoSearch (USA). The test substance may be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. Methods for the synthesis of molecular libraries are well known in the art, for example, DeWitt et al., *Proc. Natl. Acad. Sci. U.S.A.* 90, 6909, 1993; Erb et al. *Proc. Natl. Acad. Sci. U.S.A.* 91, 11422, 1994; Zuckermann et al., *J. Med. Chem.* 37, 2678, 1994; Cho et al., *Science* 261, 1303, 1993; Carell et al., *Angew. Chem. Int. Ed. Engl.* 33, 2059, 1994; Carell et al., *Angew. Chem. Int. Ed. Engl.* 33, 2061; Gallop et al., *J. Med. Chem.* 37, 1233, 1994.

According to the present method, certain candidates for therapeutic agents may be obtained by screening a substance which affects cell cycle progression. For instance, where a substance inhibiting cell cycle progression is screened by the present method, the substance may be used as a candidate for cancer therapeutics.

In order to analyze influences on cell cycle, where the conventional methods are used to identify and separate cells in different stages by fluorescence-activated cell sorting (FACS) assay, imaging using molecular probes, and Western blot analysis using cell cycle-dependent proteins, the methods are time-consuming, laborious, and expensive. However, since the DPV method may immediately detect relevant signals using probes so long as there is a time sufficient to occur cell synchronization, the DPV method may be very fast, easy, and economical.

According to an embodiment, the substance affecting cell cycles is determined as a candidate for an anticancer drug arresting cell cycles.

Cancer cells known as a malignant tumor are cells that are formed from the mutation of normal cells by actions or factors of oncogenic materials, and the cancer cells are divided and grown uncontrollably, forming malignant tumors, and invade nearby parts of the body.

The anticancer drug, which is a general term for chemotherapy for treating malignant tumor, is used as an agent representing anticancer activity by involving in various metabolic pathways of cancer cells. The anticancer drugs currently used in cancer treatments are classified into alkylating agents, antimetabolites, antibiotics, *vinca* alkaloids, and hormones, according to the biochemical mechanism.

In the present invention, when cells are treated with a candidate for an anticancer drug that arrests cell cycles, signals specifically shown in each phase are analyzed to easily determine that the candidate for an anticancer drug effectively blocks a stage in metabolic pathways. Accordingly, it is possible to determine effects of the anticancer drug in fast, easy, and economical manner.

The features and advantages of the present invention will be summarized as follows:

(a) The present method for determining cell cycle phase enables a fast and economical measurement as compared to the conventional techniques.

(b) Since the present method for determining cell cycle phase may determine the cell cycle phase immediately upon cell cycle synchronization, the present method may minimize errors that are likely to occur in the prolonged measurement time for analysis results.

(c) The present method for screening a substance affecting cell cycle may conduct quick and accurate research in the determination of unknown mechanism stages in the cell cycle.

(d) The present invention may effectively determine influences on cell cycles in the process for developing cancer drugs by determining a candidate for an anticancer drug arresting cell cycles.

DETAILED DESCRIPTION

The present invention will now be described in further detail by examples. It would be obvious to those skilled in the art that these examples are intended to be more concretely illustrative and the scope of the present invention as set forth in the appended claims is not limited to or by the examples.

EXAMPLES

Materials and Methods

Chemicals

Figure 9:
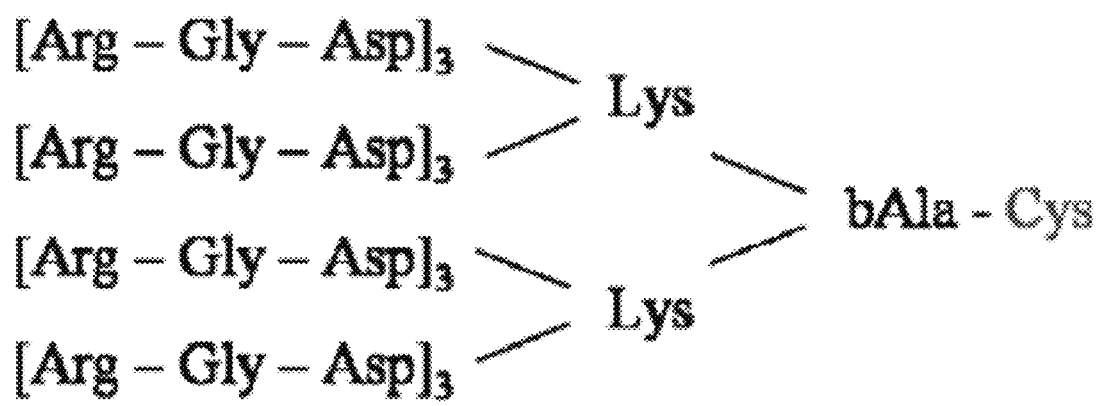
FIG. 9 represents the peptide specifically binding to integrin, which contains essentially Arg-Gly-Asp (RGD).

Thymidine and nocodazole were purchased from Sigma and used without further purification. Oligopeptide RGD-MAP-C (FIG. 9) was obtained from Peptron (Daejeon, 305-340, South Korea). RPMI 1640 Medium (RPMI 1640, purchased from Fresh Media®, Daegu, 704-230, South Korea), fetal bovine serum (FBS), antibiotics (penicillin-streptomycin, 10,000 U/ml of penicillin sodium, and 10,000 µg/ml of streptomycin sulfate in 0.83% saline), and trypsin (0.05% trypsin, 0.53 mM EDTA-4Na) were obtained from Gibco (Invitrogen, Grand Island, USA). Phosphate buffered saline (PBS) (pH 7.4, 10 mM) was purchased from Sigma-Aldrich (St. Louis, Mo., USA). Other chemicals were all of analytical grade. All solutions were prepared with double-distilled water, which was purified using a Milli-Q purification system (Branstead) to a specific resistance of >18 MΩ cm.

Preparation of Working Electrode

A silicon-based gold electrode was first cleaned with freshly prepared piranha solution (1:3 mixture of 30% $H_2O_2$ and concentrated $H_2SO_4$) for 5 min and then rinsed thoroughly with double-distilled water. The electrode was then carefully polished by sonication in absolute alcohol and double-distilled water for 5 min. Finally, the electrode was electrochemically cleaned in 0.5 M $H_2SO_4$ until a stable cyclic voltammogram was obtained and then dried with purified nitrogen. After the pretreatment, a well ordered oligopeptide (RGD-MAP-C) was fabricated on the freshly cleaned gold electrode as reported in our previous work (15). For the electrochemical measurements, a 2 cm×1 cm×0.5 cm (width×length×height) cell chip chamber was fabricated by fixing a plastic chamber (Lab-Tek®, Thermo fisher scientific, USA) to the Au working electrode using PDMS (Polydimethylsiloxane). Afterward, rat pheochromocytoma (PC12) cells were seeded on the electrode at a density of $2 \times 10^5$ cells/chip and then immobilized via RGD-integrin interaction for 24 hrs in a standard cell culture environment.

Preparation of G1/S and G2/M Block

The cell-immobilized electrode was treated with 2 mM thymidine in culture medium (RPMI 1640) for 18 hrs, followed by an 8 hrs release (replaced by fresh medium), and then again with 2 mM thymidine for another 18 hrs to block cells in G1/S-phase (FIG. 1c). Similarly, another cell-immobilized electrode was treated initially with 2 mM thymidine as mentioned before for 18 hrs, followed by a 4 hrs release (replaced by fresh medium), and then with 100 ng/ml of nocodazole for another 10 h to block cells in G2/M-phase (FIG. 1c). Therefore, the working electrodes were prepared for electrochemical signal analysis of the cells in different phases of the cell cycle. Furthermore, for the time-dependent progression of G1/S-phase towards G2/M-phase, G1/S-blocked cells were released in fresh medium containing 10% FBS for several hours to perform electrochemical measurements.

Electrochemical Measurements

Figure 7:
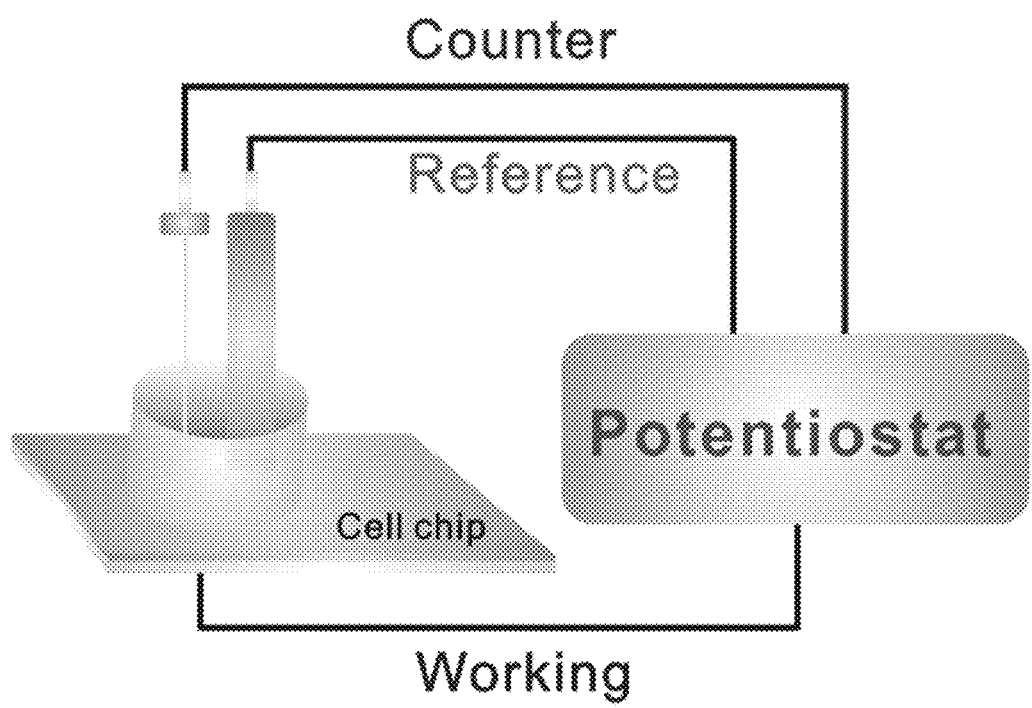
FIG. 7 represents the image of the fabricated RGD-MAP-C based-cell chip and tri-electrode system for measuring cell cycles electrochemically.
Figure 8:
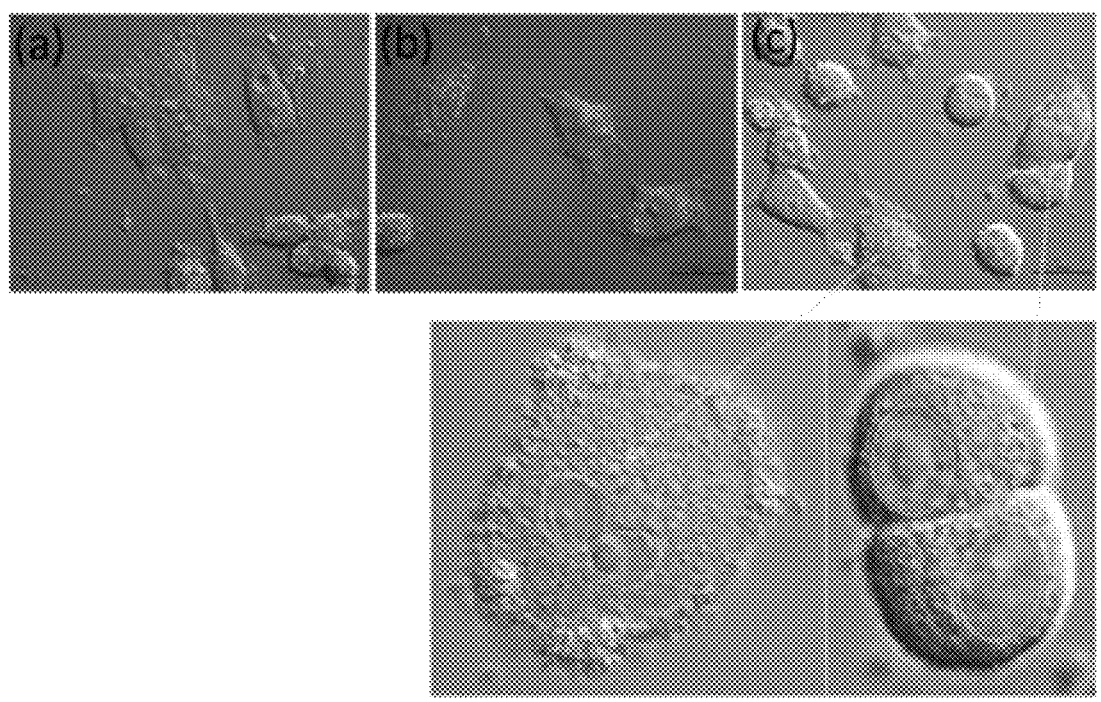
FIG. 8a represents unsynchronized cells containing all the phases of the cycle. However, only G1/S Phases in FIG. 8b and mitotic phases in FIG. 8c were achieved from artificially synchronized chip.

Electrochemical measurements were carried out with a CHI660C Potentiostat (CH Instruments). The commonly used three-electrode configuration was employed for the electrochemical measurements, whereas standard silver (Ag/AgCl) served as the reference and a platinum wire as the counter electrode (FIG. 7). Prior to the electrochemical measurements, a gold electrode with G1/S and G2/M-phase cells was washed twice with 10 mM PBS buffer (pH 7.4). Finally, electrochemical measurements were performed using 2 ml of the same PBS solution as the electrolyte. Before the measurements, the buffer solution was first thoroughly bubbled with high purity nitrogen for 30 min. Then, a stream of nitrogen was blown gently across the surface of the solution in order to prevent exposure to aerobic oxygen throughout the experiment. In order to minimize the scan effect, several repeated scans were performed and DPV signal from $3^{rd}$ scan was selected for all the measurements throughout the study. Moreover, all measurements were performed independently at least three times, and error bars are shown in the figures.

Fluorescence-Activated Cells Sorting (FACS) Analysis

Thymidine and nocodazole-treated synchronized cells were collected and fixed by re-suspension in 0.5 ml of 70% ethanol for 30 min, followed by centrifugation at 1,000 rpm for 10 min and washing in ice-cold PBS. The resulting cell pellets were then re-suspended in 0.5 ml of PBS containing 50 μg/ml of propidiumiodide (Sigma-Aldrich Chemical Co., St. Louis, Mo.) and 100 μg/ml of RNase (Invitrogen, Carlsbad, Calif.), followed by incubation at 37° C. for 30 min. Cell-cycle distribution was examined by measuring DNA content using a flow cytometer (FACS Caribur flow cytometer, Becton Dickinson, San Jose, Calif.) as described previously (24). A minimum of $10^4$ cells per data point was subjected to examination. The regions marked M1, M2, and M3 represent G1, S, and G2/M-phase of the cell cycle, respectively.

Protein Assay

The synchronized PC12 cell pellet was solubilized for 15 min at 4° C. in lysis buffer. Lysates were centrifuged at 13,000 g for 30 min at 4° C. in order to remove insoluble material. The supernatant was then collected, and the protein concentration was determined using BCA protein assay reagent (Pierce Chemicals). For Western blot analysis, samples (25 μg each) were separated by electrophoresis on SDS-polyacrylamide gels (12% for actin and cyclin B1, 16% for p-HH$^3$) and then transferred onto polyvinylidene difluoride membranes (Bio-Rad). The membranes were probed with anti-p-HH$^3$ (1:2000; Cell Signaling), anti-cyclin B1 (1:2000; Abchem), and anti-β-actin (A-5441, 1:10,000). The membranes were incubated with the respective antibodies at 4° C. overnight. After three washes with PBS containing 0.015% (vol/vol) Tween-20 for 10 min each, the membranes were incubated with secondary antibody (antimouse IgG-HRP for actin, anti-rabbit IgG-HRP for cyclin B1 and p-HH$^3$) for 1 hr at room temperature. The membranes were washed again three times and then developed using enhanced chemiluminescence (Amersham Biosciences, Uppsala, Sweden).

RESULTS AND DISCUSSION

Figure 1A:
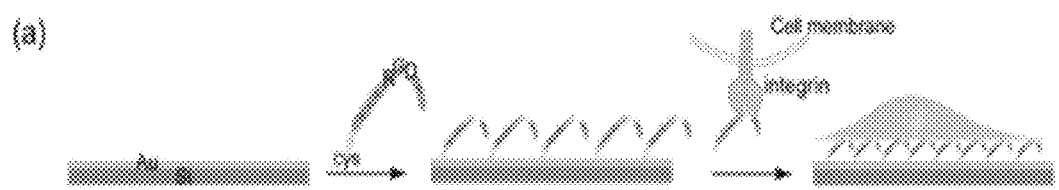
FIG. 1 represents schematics of experimental setup: (a) fabrication of RGD-MAP-C based-cell chip used throughout the experiments; (b) synchronized G1/S-phase (middle), G2/M-phase (right), and unsynchronized (left) cells with their respective DPV signals (down arrows indicate respective signals); and (c) time course of cell treatment for synchronization in G1/S-phase (i) and G2/M-phase (ii), and gradual progression of G1/S cells towards G2/M-phase following time-dependent release from G1/S block (iii).
Figure 1B:
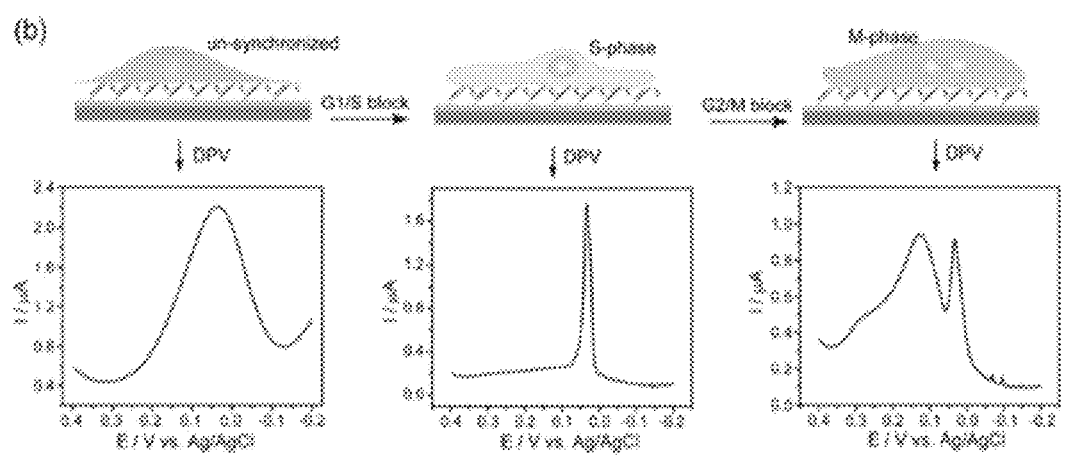

FIG. 1a illustrates the fabrication process of the cell-attaching electrode (Au/RGD-MAP-C/cell) used for the cell chip. RGD-MAP-C peptide containing a cysteine residue at its terminus was self-assembled on an Au electrode via an Au—S covalent bond, which results in strong attachment of cells to the electrode surface (14, 15). Cell immobilization on a peptide-modified surface leads to establishment of strongly-linked integrin receptors on the cell surface (15, 25). The enhanced binding affinities of the cellular receptors to the electrode surface prevent cell detachment caused by washing throughout the experiment, and they also enhance electron transfer during the electrochemical measurements (16). The unsynchronized cells were then subjected to double thymidine treatment (18 hrs for each) with 8 hrs release by replacing the thymidine-containing media with fresh RPMI 1640, which converted the cells to G1/S-phase (FIG. 1c). Similarly, cells in G2/M-phase were produced by treatment with thymidine for 18 hrs with 4 hrs release, followed by treatment with nocodazole for 10 hrs. Consequently, the different electrochemical characteristics of the cells in G1/S, G2/M, or unsynchronized phase were measured to monitor the intensity or potential difference in voltammetry (FIG. 1b).

Electrochemical Characterizations of Fabricated Cell Chip

Figure 2:
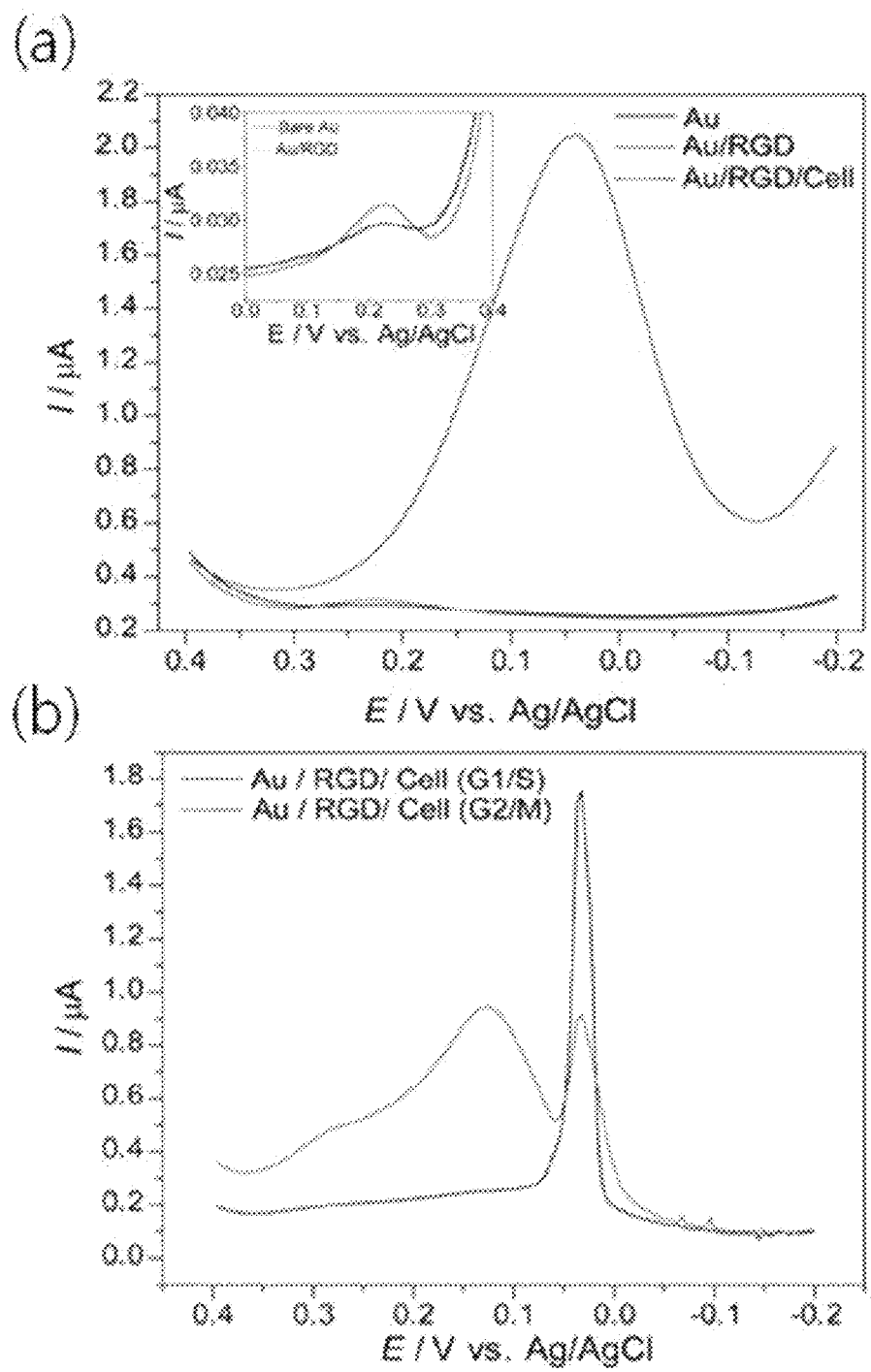
FIG. 2 represents electrochemical characterization of fabricated cell-based chip: (a) DPV signals measured from bare Au, peptide-fabricated Au, and cell-immobilized peptide-fabricated electrode (inset shows the signal differences between bare Au and Au/RGD), (b) DPV signals measured from the chip synchronized in G1/S-phase and G2/M-phase. DPV was measured using PBS (0.01 M, pH 7.4) as an electrolyte at a scan rate of 100 mVs$^{-1}$. Pulse amplitude and pulse width were 50 mV and 50 ms, respectively. The whole experiment was conducted at a temperature of 27±1° C. using Pt and Ag/AgCl as counter and reference electrodes, respectively.

The step-by-step surface modification of the Au electrode surface (FIG. 1a) was further characterized electrochemically by the DPV method as shown in FIG. 2a. A strong cathodic peak current appeared ($I_{pc}$) at +75 mV from the Au/RGD-MAP-C/Cell electrode (FIG. 2a); however, a very weak peak or no peak was observed from the bare Au or Au/RGD-MAP-C electrode (inset of FIG. 2a), which represents the redox reaction of the cells in our system. When the cells immobilized on the Au electrode were exposed to thymidine/thymidine for G1/S-phase block, a sharp electrochemical signal appeared at +50 mV (FIG. 2b), which was different from that of the unsynchronized cells. Remarkably, a new peak was observed at +150 mV during DPV measurement of the cells, which were treated with thymidine/nocodazole for G2/M-phase block (FIG. 2b). These differences in DPV signaling from identical cells in different phases (G1/S, G2/M) may have been due to changes in the redox properties of morphologically-altered cells (26). It is well known that double thymidine treatment blocks the cell cycle in the synthesis phase (27, 28), where DNA replication occurs (29) and causes remarkable alteration of the cell nucleus (30). Similarly, thymidine/nocodazole pauses the cell cycle in M-phase, (28, 31, 32) where the nucleus becomes divided into two daughter cells (33). Therefore, the specific DPV signals from cells in G1/S and G2/M-phase, which is completely different from unsynchronized cells, may be employed as a tool for the determination of cell cycle arrest.

Confirmation of Cell Synchronization

Figure 3:
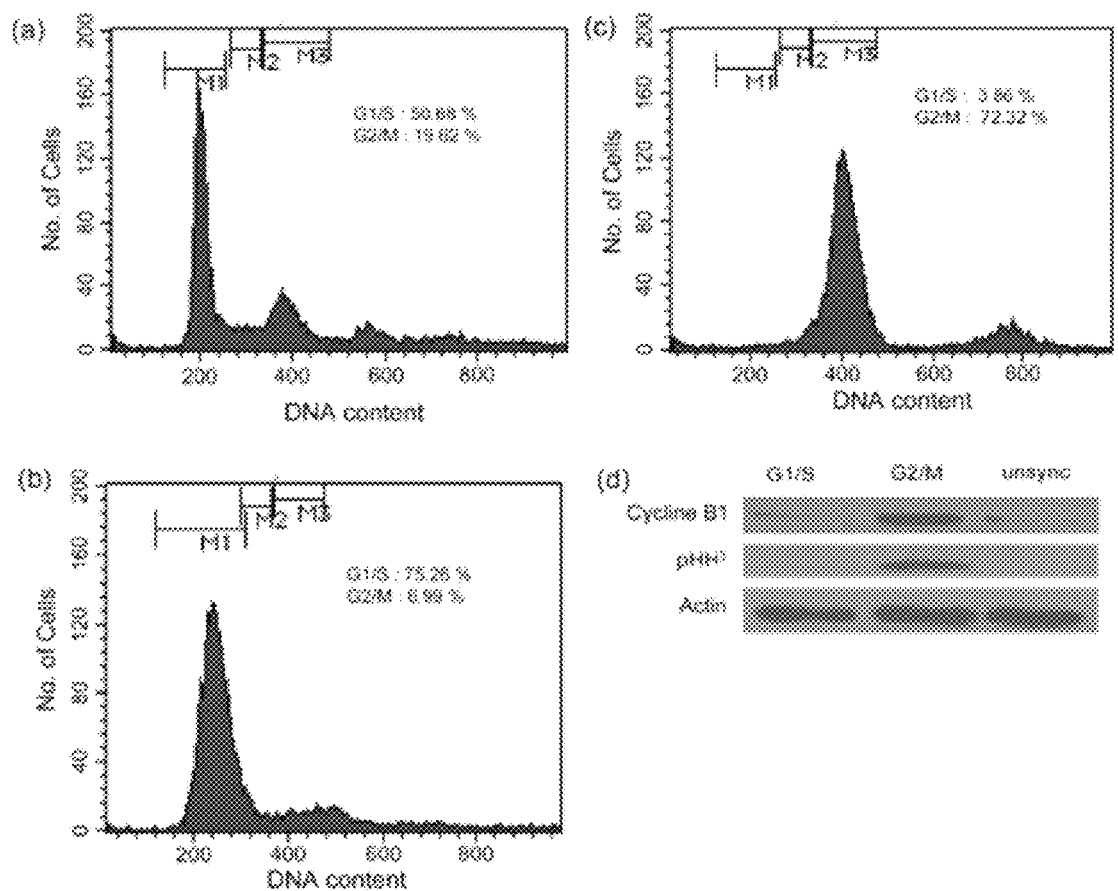
FIG. 3 represents confirmation of thymidine and/or nocodazole-mediated cell cycle arrest at G1/S-phase and G2/M-phase: FACS data show (a) unsynchronized cells in all phases of cell cycle but mostly G1, (b) cells in G1/S block, with cells mostly in G1 and S-phase and decreased in M-phase, (c) cells in G2/M block, with cells mostly G2 and M-phase and decreased in other phases. Similarly, (d) Western blot assay shows expression of Phospho-Histone H$^3$ (pHH$^3$) in G2/M-phase cells but not in G1/S-phase or unsynchronized cells, and the highest intensity of cyclin B1 was observed in G2/M-phase cells compared to other phases, indicating that most of the cells converted to G2/M-phase.

On-chip synchronization of PC12 cells was confirmed by both of conventional fluorescence-assisted cell sorting (FACS) (34, 35), Western blot analysis using phase-specific proteins (FIG. 3c), and optical microscopy. The results show that PC12 cells were successfully synchronized using thymidine and/or nocodazole treatment. Approximately 75% of the cells were fixed in G1/S-phase (FIG. 3b) and 72% were synchronized in G2/M-phase (FIG. 3c), depending on the time of chemical exposure, respectively. On-chip cell synchronization was further confirmed by Western blot analysis using G2/M-phase specific protein phosphohistone (p-HH$^3$) (36-38) and cyclin B1 (39-41). FIG. 3d shows that p-HH$^3$ was expressed in G2/M-phase but absent in unsynchronized and G1/S-blocked cells, whereas cyline B1 was expressed dominantly in G1/S-phase cells (39, 41). These results prove that the cells were successfully synchronized on the chip.

Monitoring of Cell-Cycle Progression Based on Electrochemical Method

Figure 4:
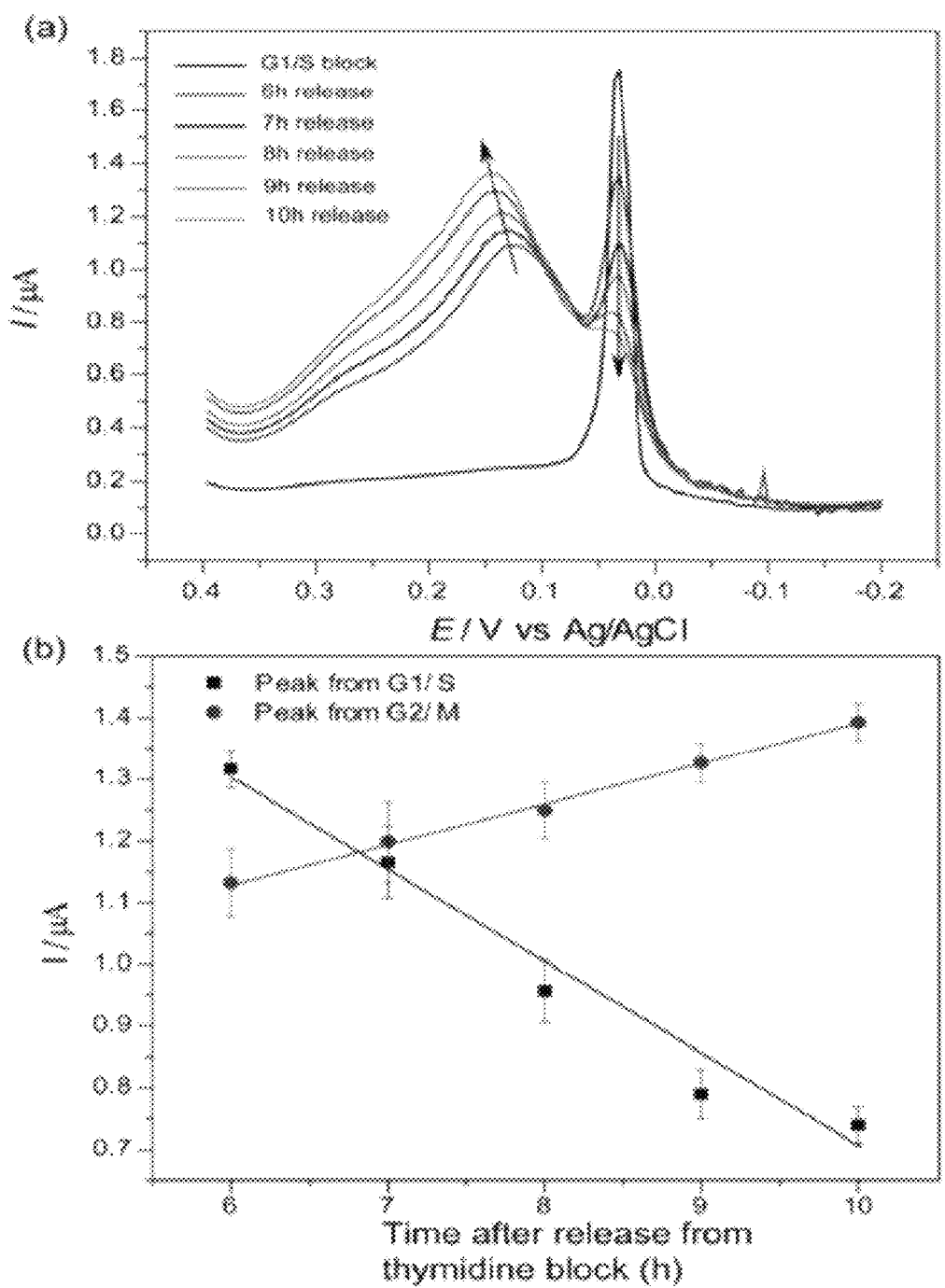
FIG. 4 represents time-dependent progression of G1/S-phase towards G2/M-phase: (a) changes in DPV current peak intensities of PC12 cells after several hours (from 2 h to 10 h) of release from G1/S block, where (↓) arrow indicates decreased peak from G1/S-phase and (↑) arrow indicates increased peak from G2/M-phase, (b) A black-colored line indicates linearly decreased current peak ($I_{pc}$) from G1/S-phase in a time-dependent manner ($R^2$=0.99), whereas red-colored line indicates linearly increased current peak ($I_{pc}$) from G2/M-phase in a time-dependent manner ($R^2$=0.96). Data are the mean±standard deviation of three different experiments.
Figure 5A:
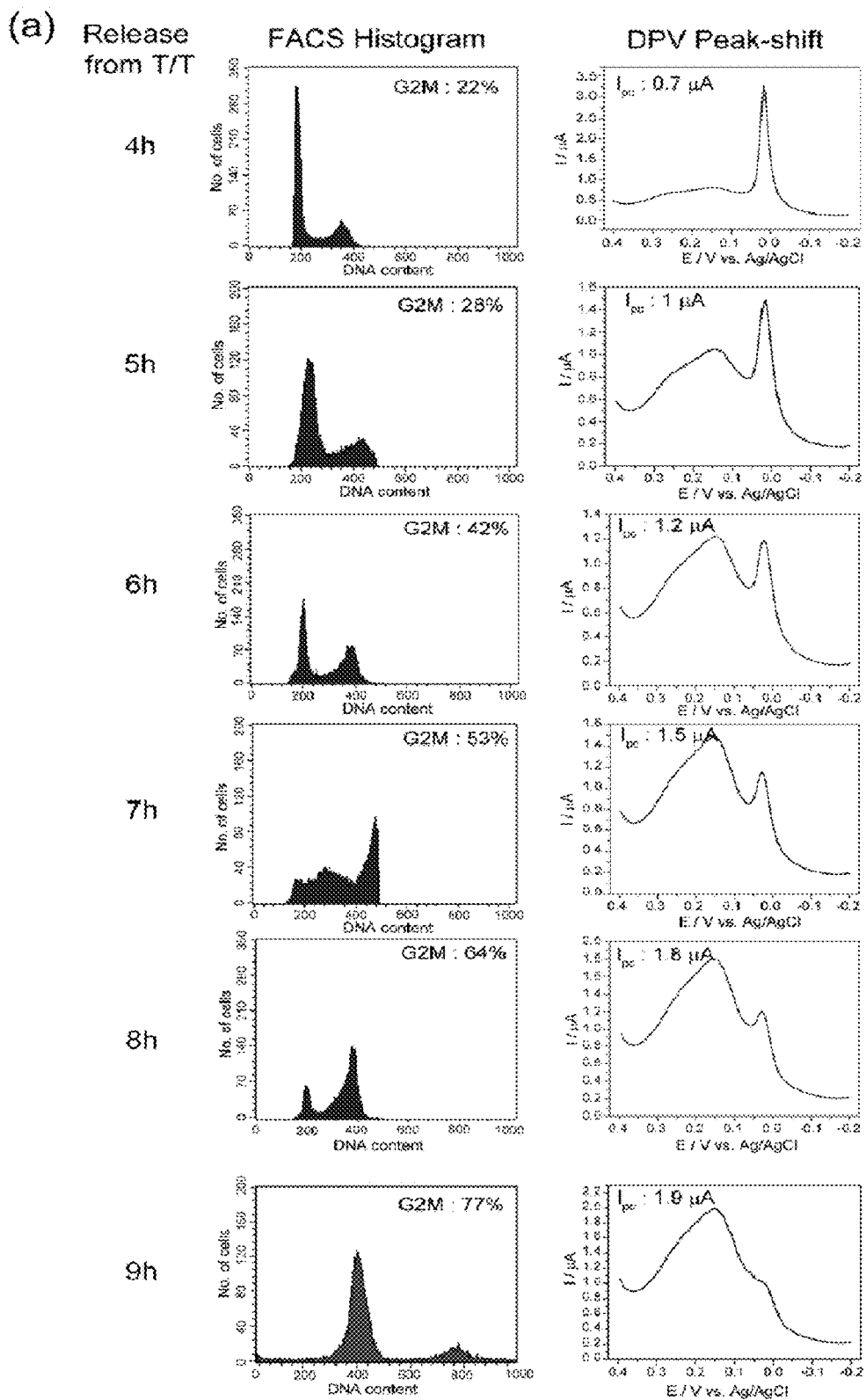
FIG. 5 represents that (a) Validation of electrochemical determination of progression of G1/S-phase cells towards G2/M-phase using FACS (Left row), and changes in DPV current peaks (Right row) of PC12 cells, several hours (from 2 h to 10 h) post-release from G1/S block, (b) dependence of DPV peak intensities measured from G2/M (red line) and % G2/M-phase cells as measured by FACS (blue line) during the release from double thymidine induced G1/S block. Data are the mean±standard deviation of three different experiments.
Figure 5B:
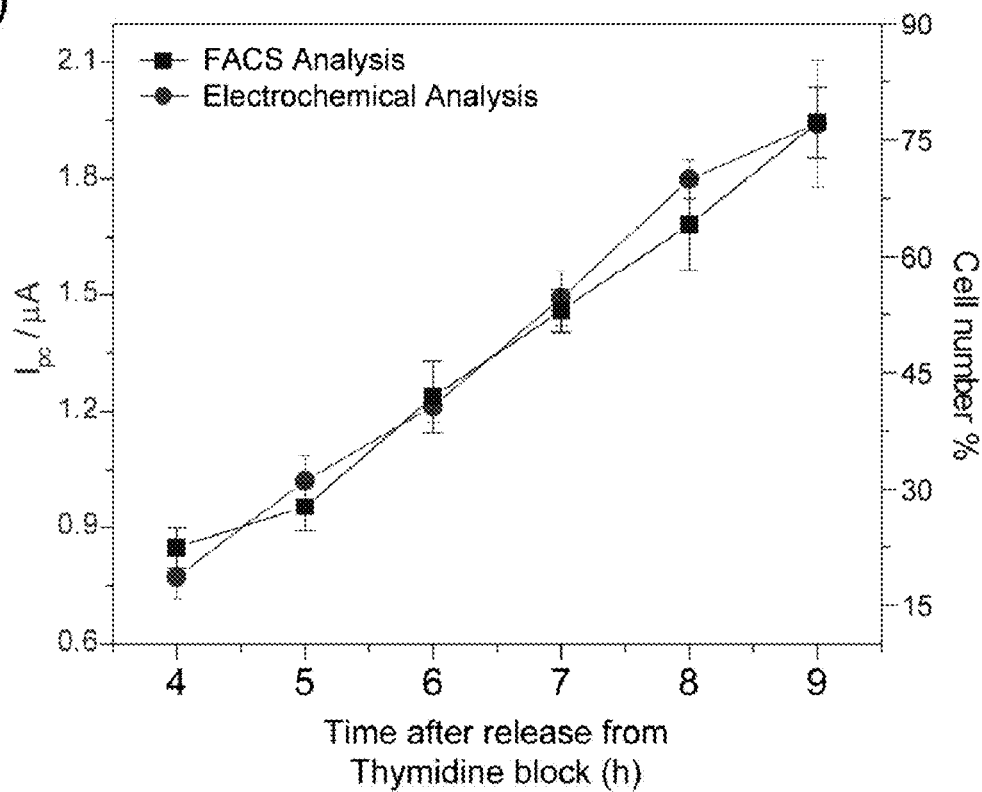

After confirmation of cell cycle arrest using conventional methods, the cell chip containing a Au/RGD-MAP-C/Cell electrode was employed to measure time-dependent electrochemical characteristics during cell cycle progression. Thymidine-induced G1/S-blocked cells were released for several hours (6, 7, 8, 9, and 10 hrs), and electrochemical measurements were performed at each release time (FIG. 4a). The cells in G1/S-phase produced a sharp peak at a potential of +50 mV, but G2/M-phase cells gave an additional peak at +150 mV that increased with the time of release from double thymidine treatment (FIG. 4a). This suggests that G1/S-phase cells progressed to G2/M-phase as the release period increased. Interestingly, the peak at +50 mV produced by G1/S-phase cells decreased as the new peak increased at +150 mV, which indicates that the new peak was directly related to the number of cells in G2/M-phase. Moreover, opposite linearity was observed after analyzing and quantifying the DPV peak currents measured from the G1/S and G2/M-phase synchronized chip (FIG. 4b). This indicates that G1/S-phase cells gradually progressed to G2/M-phase as the release period increased. Conversion to G2/M-phase was observed from 6 h after release, whereas maximum conversion occurred after 10 h of release (FIG. 4b). This finding is in agreement with a previous study (6, 42) that reported G1/S-phase cells are completely converted to G2/M-phase after 9 to 10 hrs of release from double thymidine block. It is well known that release from G1/S block allows cells to progress into M-phase for nuclear division and ultimately cell division (14). During this phase, cells pass through a number of complex processes, including prophase, prometaphase, metaphase, anaphase, and telophase, which lead to several changes in the nucleus (6, 43). These cytological changes might be responsible for alterations in the electrochemical behavior of the cell. Therefore, the electrochemical signal is certainly reasonable, based on the observation that the new peak appears as the cell approaches M-phase and the intensity is increased due to a higher number of cells in G2/M-phase. Therefore, quantification of the synchronized cells was performed indirectly but accurately by analyzing the current peak obtained from DPV signal intensities using our newly developed electrochemical method.

Validation of Newly Developed Electrochemical Cell-Cycle Monitoring

Time-dependent progression of G2/M-phase was monitored by both conventional FACS (34) and our newly developed electrochemical method. Here, the DPV peak indicating G2/M-phase appeared when cells were released from G1/S block, and the peak increased upon a longer period of release with a corresponding decrease in the initial peak, which is in agreement with previous data. Similarly, the histograms obtained from FACS show that the number of cells in G1/S-phase decreased, which increased the number of cells in G2/M-phase as the release period increased. Therefore, DPV peak behavior according to time of release from G1/S-phase was in agreement with the data obtained by the conventional FACS method. Moreover, the trend line derived from analyzing and quantifying the peak current ($I_{pc}$) value increased from the time of release from G1/S block and achieved a maximum at 10 hrs post-release. A similar trend line was also reported by analyzing the numbers of cells that progressed to G2/M-phase by FACS. Therefore, our data obtained by the newly developed electrochemical method completely coincided with conventional FACS assay. Therefore, the results of the electrochemical signal using by this cell-based electrochemical chip were valid. By using this electrochemical technology, we were able to detect cells in each phase by analyzing and quantifying their DPV signal intensities.

Figure 6:
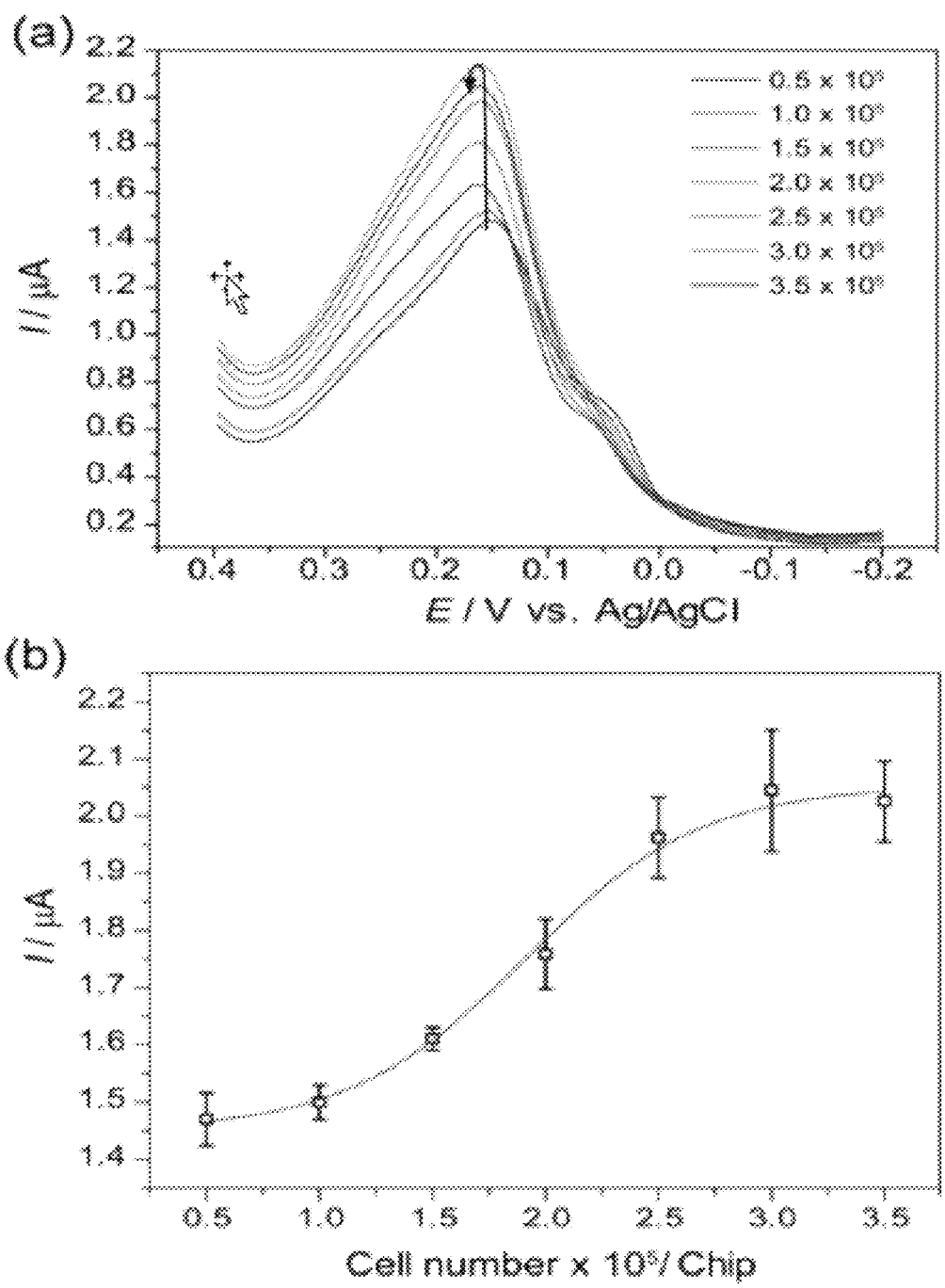
FIG. 6 represents reproducibility of electrochemical cell-cycle determination using varying numbers of cells: (a) Changes in DPV peak intensities corresponding to the various concentrations of PC12 cells on the chip surface (from 0.5×10$^5$ cells/ml to 3.5×10$^5$ cells/ml), (↑) arrow indicates the increases in peak currents with increasing cell numbers. Cells were synchronized in G2/M-phase by releasing cells from G1/S block after 10 h for electrochemical recording, (b) a typical sigmoid curve indicates the linear increases in current peaks ($I_{pc}$) in a concentration-dependent manner ($R^2$=0.99). Data are the mean±standard deviation of three different experiments.

Reproducibility of Electrochemical Cell-Cycle Determination Using Varying Numbers of Cells The number of cells immobilized on each chip was determined to improve the sensitivity of detection as well as to verify reproducibility. For this, varying numbers of cells starting from $0.5 \times 10^5$ cells/ml to $3.5 \times 10^5$ cells/ml were allowed to synchronize following the protocol discussed above, and electrochemical measurements were performed accordingly. FIG. 6a shows that the current response increased with increasing cell numbers. A concentration-dependent sigmoid curve ($r^2=0.99$) was obtained between the current responses and cell numbers (FIG. 6b). The concentrations of cells from $1 \times 10^5$ cells/ml to $3 \times 10^5$ cells/ml gave exponentially increased signals, whereas decreased signals/nonspecific signals/no signals were observed from the concentrations of cells between $3.5 \times 10^5$ cells/ml to $4.5 \times 10^5$ cells/ml. This phenomenon was occurred due to improper synchronization of cells in high density compared to the space of the chip surface (44). From these results, we found the optimal concentrations of cells ($3 \times 10^5$ cells/ml) for the successful cell synchronization and for achieving maximum signal intensities (FIG. 6a). The relative standard deviation of the DPV peak for seven different concentrations of cells was 5.6%, indicating that the electrochemical cell chip had high sensitivity and reproducibility for cell cycle synchronization.

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

REFERENCES (1) Hartwell, L. H. et al., Science 1989, 246, 629-634.
(2) Alberts, B. et al., The molecular biology of the cell. Garland Science, Taylor & Fransis Group, New York, 2002.
(3) Smith, J. A.; Martin, L. Proc. Natl. Acad. Sci. U.S.A. 1973, 70, 1263-1267.
(4) Nelson, D. M. et al., Mol. Cell. Biol. 2002, 22, 7459-7472.
(5) Nyberg, K. A. et al., Annu. Rev. Genet. 2002, 36, 617-656.
(6) Cude, K. et al., Cell Biol. 2007, 177, 253-264.
(7) Li, F. et al., Nature 1998, 396, 580-584.
(8) Leung, B. S. et al., J. Cell. Biochem. 1987, 34, 213-225.
(9) Bowen, W. P. et al., Assay Drug Dev. Technol. 2006, 4, 209-221.
(10) Samaké, S.; Smith, L. C. Theriogenology 1997, 48, 969-976.
(11) Xiang, Y. et al., Nature Methods 2009, 6, an2-an3.
(12) Wong, J. T. Y. et al., Exp. Marine Biol. and Ecol. 1996, 197, 91-99.
(13) Nunez, R. Mol. Biol. 2001, 3, 67-70.
(14) Jin H. S.; Lee, T. H. Biochem. J. 2006, 399, 335-342.
(15) Kafi, M. A.; Kim, T. -H.; Yea, C. -H.; Kim, H.; Choi, J. -W. Biosens. Bioelectron. 2010, 26, 1359-1365.
(16) Kafi, M. A.; Kim, T. -H.; Yagati, A. K.; Kim, H.; Choi, J. -W. Biotechnol. Lett. 2010, 32, 1797-1802.
(17) El-Said, W. A.; Yea, C.; Kim, H.; Oh, B. K.; Choi, J. -W. Biosens. Bioelectron. 2009a, 24, 1259-1265.
(18) El-Said, W. A.; Yea, C. -H.; Kwon, I. -K.; Choi, J. -W. Biochip J. 2009b, 3, 105-112.
(19) Choi, J. W.; Nam, Y. S.; Fujihira, M. Biotechnol. Bioprocess. Eng. 2004, 9, 76-85.
(20) May, K. M.; Wang, Y.; Bachas, L. G.; Anderson, K. W.; Anal. Chem. 2004, 76, 4156.
(21) Yea, C. H.; Min, J.; Choi, J. W. Biochip J. 2007, 1, 219-227.
(22) Wang, L.; Wang, L.; Yin, H.; Xing, W.; Yu, Z.; Guo, M.; Cheng, J.; Biosens. Bioelectron. 2010, 25, 990-995.
(23) Gutierrez, G. J. et al., Biol. Chem. 2010, 285, 14217-14228,
(24) Zhu, H. et al., Cancer Res. 2000, 60, 1283-1289.
(25) Ruoslahti, E. Annu. Rev. Cell Dev. Biol. 1996, 12, 697-715.
(26) Mitchison, T. J.; Salmon, E. D. Nat. Cell Biol. 2001, 3, E17-E21 doi:10.1038/35050656
(27) Huberman, J. A. Cell 1981, 23, 647-648.
(28) Zhu, H.; and Nigel, J. Toxicol. Sci. 2006, 91, 132-139.
(29) McCulloch, S. D.; Kunkel T. A. Cell Res. 2008, 18, 148-161.
(30) Lengronne, A.; Pasero, P.; Bensimon, A.; Schwob, E. Nucleic Acids Res. 2001, 29, 1433-1442.
(31) Krek, W.; DeCaprio, J. A. Methods Enzymol. 1995, 254, 114-124.
(32) Zieve, G. W.; Turnbull, D.; Mullins, J. M.; McIntosh, J. R. Exp. Cell Res. 1980, 126, 397-405.
(33) Reddy, G. P. J. Cell. Biochem. 1994, 54, 379-386.
(34) Resnitzky, D. et al., Mol. Cell. Biol. 1994, 14, 1669-1679.
(35) Futcher, B. Methods in Cell Science 1999, 21, 79-86.
(36) Kaitna, S. et al., Biol. 2002, 12, 798-812.
(37) Cortez, D. et al., Science 2001, 294, 1713-1716.
(38) Crosio, C. et al., Mol. Cell. Biol. 2002, 22, 874-885.
(39) Cogswell, J. P. et al., Mol. Cell. Biol. 1995, 15, 2782-2790.
(40) Norbury, C.; Nurse, P. Annu. Rev. Biochem. 1992, 61, 441-470.
(41) Pines, J.; Hunter, T. Cell 1989, 58, 833-846.
(42) Langan, T. J.; Slater, M. C.; Kelly, K. Glia. 1994, 10, 30-39.
(43) Huang, J. N.; Park, I.; Ellingson, E.; Littlepage, L. E.; Pellman D. J. Cell Biol. 2001, 154, 85-94.
(44) Bartholomew, J. C.; Neff, N. T.; Ross, P. A. J. Cell Physiol. 1976, 89, 251-258.

What is claimed is:

1. A method for determining cell cycle phase, comprising:
   (a) immobilizing a capture agent on a substrate wherein the capture agent specifically binds to a cell membrane protein and wherein the cell membrane protein is a binding partner to the capture agent;
   (b) binding a cell having the cell membrane protein as the binding partner to the capture agent;
   (c) treating the cell with a cell cycle synchronizing agent; and
   (d) measuring a redox potential of the cell,
   wherein the step (d) is performed by a differential pulse voltammetry using a tri electrode consisting of a working electrode, a reference electrode, and a counter electrode, and
   wherein where a peak was observed only at 50 mV in the redox potential, the cell cycle phase is determined to be in the G1/S phase; where a peak was observed only at 150 mV in the redox potential, the cell cycle phase is determined to be in the G2/M phase; where peaks are observed at 50 mV and 150 mV in the redox potential, if the magnitude of the peak at 50 mV decreases and the magnitude of the peak at 150 mV increases with time, the cell cycle phase is determined to be in the transition from G1/S to G2/M phase is in progress; if the magnitude of the peak at 50 mV increases and the magnitude of the peak at 150 mV decreases, the cell cycle phase is determined to be in the transition from G2/M to G1/S is in progress.

2. The method according to claim 1, wherein the cell membrane protein is integrin.

3. The method according to claim 1, wherein the capture agent is a peptide, a protein, an antibody or an aptamer.

4. The method according to claim 1, wherein the substrate is coated with gold (Au).

5. The method according to claim 1, wherein the cell cycle synchronizing agent is thymidine, aphidicolin, colchicine, nocodazole or 5-fluorodeoxyuridine.

6. A method for screening a substance affecting cell cycles, comprising:
   (a) immobilizing a capture agent on a substrate wherein the capture agent specifically binds to a cell membrane protein and wherein the cell membrane protein is a binding partner to the capture agent;
   (b) binding a cell having the cell membrane protein as the binding partner to the capture agent;
   (c) treating the cell with a test substance of interest for analysis; and
   (d) measuring a redox potential of the cell,
   wherein the step (d) is performed by a differential pulse voltammetry using a tri electrode consisting of a working electrode, a reference electrode, and a counter electrode, and
   wherein when the test substance changes the redox potential compared to the redox potential of a cell treated with a cell cycle synchronizing agent, it is determined to be a substance affecting cell cycles.

7. The method according to claim 6, wherein the cell membrane protein is integrin.

8. The method according to claim 6, wherein the capture agent is a peptide, a protein, an antibody or an aptamer.

9. The method according to claim 6, wherein the substrate is coated with gold (Au).

10. The method according to claim 6, wherein the substance determined to affect cell cycles is a candidate for an anticancer drug arresting cell cycles.

11. The method according to claim 6, wherein the cell cycle synchronizing agent is thymidine, aphidicolin, colchicine or 5-fluorodeoxyuridine.

12. The method according to claim 6, wherein the method further comprises a step treating the cell with a cell cycle synchronizing agent between the steps (b) and (c).

* * * * *